United States Patent [19]

Fleischhacker

[11] Patent Number: 5,092,857
[45] Date of Patent: Mar. 3, 1992

[54] HEMOSTASIS VALVE HAVING SUPPORT SHOULDERS

[76] Inventor: John J. Fleischhacker, 14901 Minnetonka Industrial Rd., Minnetonka, Minn. 55345

[21] Appl. No.: 702,239

[22] Filed: May 17, 1991

[51] Int. Cl.$^5$ ............................................. A61M 5/00
[52] U.S. Cl. .................................. 604/256; 604/167; 137/846; 251/149.1
[58] Field of Search ............... 604/256, 167, 169, 164; 251/149.1; 137/846, 847, 848, 849, 850

[56] References Cited

U.S. PATENT DOCUMENTS 4,436,519 3/1984 O'Neill ........................... 604/256 X
4,909,798 3/1990 Fleischhacker et al. ........ 604/167 X Primary Examiner—John J. Wilson
Assistant Examiner—Jeffrey A. Smith
Attorney, Agent, or Firm—Scott R. Cox

[57] ABSTRACT

Disclosed herein is a hemostasis valve which is formed of a longitudinally extended valve housing having a first opening and a central longitudinal passage communicating with an opposite second opening. A cap is provided for enclosing the first opening of the housing, said cap having a hole to permit insertion of a catheter. Also provided is a one-piece seal located within the longitudinally extended housing, said seal comprising a sealing neck having a relatively small opening therein, communicating with a sealing chamber having opposing sealing exit lips which are both readily expandable and support shoulders on the outside of said seal adjacent to the sealing neck to provide support for the seal.

8 Claims, 2 Drawing Sheets

HEMOSTASIS VALVE HAVING SUPPORT SHOULDERS

BACKGROUND OF INVENTION

1. Field of Invention

This invention relates to hemostasis valves. More particularly, this invention relates to an improved hemostasis valve with support shoulders which is useful with a variety of catheters.

2. Prior Art

The introduction of catheters into blood vessels for a variety of purposes such as coronary angiography has been known for many years. Several techniques for introducing these catheters are available. One such technique is the cut-down method. Another is the Seldinger technique. This technique involves surgically opening a vein or artery with a needle, inserting a guidewire into the vein or artery through the lumen of the needle, withdrawing the needle, inserting over the guidewire a dilator located inside an associated sheath with a hemostasis valve, removing the dilator and inserting a catheter through the sheath and into the blood vessel.

Various types of hemostasis valves have been known in the prior art. However, in most cases each hemostasis valve is designed for use with a specific size of catheter. Because adequate sealing around the catheter walls cannot be obtained for a variety of catheters having various diameters using conventional hemostasis valves, it has not been possible to employ a single hemostasis valve with catheters of widely varying diameters.

These problems are particularly acute when the guidewire technique is used. Guidewires are of extremely small diameter-often less than 0.050 inch. However, many catheters are relatively much larger in diameter. Therefore, in the prior art it has been difficult to design hemostasis valve which will seal around both relatively large diameter catheters as well as relatively small diameter guidewires.

One method of solving this particular problem is shown in U.S. Pat. No. 4,909,798 which discloses a universal hemostasis cannula with hemostasis valve contained within a longitudinally extended valve housing having a first opening and a central longitudinal passage communicating with the opposite second opening. This valve has solved some of the problems relating to the extremely small diameter of the guidewires with the relatively larger diameter of the catheters, catheter introducers and dilators.

Other devices designed to solve the problem of various sizes of catheters introduced as part of a surgical procedure have been disclosed for example, in U.S. Pat. No. 4,000,739 which employs two gaskets to seal against the back pressure of blood in the cannula unit. The first, donut-shaped, gasket is provided with a hole slightly smaller than the diameter of the catheter to be inserted, while the second gasket is provided with a Y-shaped slit. However, when guidewires or catheters which are too small in diameter are inserted into this hemostasis valve, the sealing advantages of the first, donut-shaped gasket are no longer available because the larger diameter donut hole will not seal around the smaller diameter guidewire or catheter. Moreover, when catheters are employed having diameters which are extremely large in relation to the diameter of the hole in the donut-shaped gasket, the gasket may become separated from the hemostasis valve body or it may be unduly stretched so that it will not seal properly when a smaller sized catheter is inserted at a later time.

Hemostasis valves having similar problems are disclosed in U.S. Pat. Nos. 4,673,393 and 4,610,665.

U.S. Pat. No. 4,436,519 discloses a combination of a donut-shaped gasket and a second cup-shaped seal. Like the prior art, two gasket hemostasis valves described above, the device described in the '519 patent suffers the same deficiencies because its donut-shaped gasket can only accept catheters having a limited range of diameter sizes. Moreover, this device is particularly susceptible to leakage when only the guidewire is in place.

U.S. Pat. No. 4,341,239 discloses a combination check-over pressure relief valve similar in design to the '519 device containing a cylindrical main body portion which is supported by a radially outwardly extending flange and as a stiffening means, ribs wherein said ribs project from the surface of the main body portion.

U.S. Pat. No. 4,655,752 discloses a surgical cannula which does not employ donut-shaped gaskets. However, this cannula, like the other prior art cannulas, suffers from a lack of universality and from poor sealing. While two seals are employed, the second seal may only be used with catheters having a limited range of diameters and will provide little or no sealing for a guidewire.

German Patent No. 3,042,229 purports to describe a hemostasis valve which may be used with catheters having a variety of diameters. However, it is extremely difficult to use this valve when relatively large diameter catheters are employed because the second seal, as shown in the patent, is required to expand against the sidewalls of the cannula, thereby, significantly increasing friction during insertion and the risk of hemodynamic dampening. Moreover, the sealing means of the device described in the '229 patent is formed from two separate pieces thereby increasing the difficulties of manufacture and the likelihood that one of the seals may become dislodged particularly during use with large sized catheters. See also U.S. Pat. No. 4,809,679.

Another problem shown by many prior art hemostasis cannulas is that the cardiologist must be able to "feel" the catheter as it is inserted through the gaskets or other sealing members of the hemostasis valve and ultimately into a blood vessel. If insertion of the catheter through the hemostasis valve is too difficult, the cannula unit may be rejected by cardiologists as being difficult to use during catheter insertion. Concomitantly, the use of hemostasis valves which exert undue pressure on the side walls of inserted catheters may lead to excessive hemodynamic dampening of the catheter. In other words, excessive pressure on the exterior sidewalls of a catheter may cause a narrowing of the catheter's diameter thereby altering measurement parameters within the catheter.

In addition, hemostasis valves have also experienced problems from collapse of a portion or portions of the valve during the withdrawal of the dilator and the insertion of the catheter. Further, repeated insertion and withdrawal of catheters and catheter related devices through conventional hemostasis valves has become more and more difficult. This increase in force necessary for insertion and withdrawal further reduces the usability of conventional hemostasis valves.

Thus, it is important in providing a sealing mechanism for a hemostasis valve unit such that the unit:

1. is universal, i.e., useful with both guidewires and with catheters having a wide range of diameters;
2. provides relatively easy insertion and withdrawal of all diameters of catheters;
3. is free from excessive restriction which would cause hemodynamic dampening; and
4. has sufficient strength not to collapse on the insertion and removal of the various medical devices during the introduction of catheters into blood vessels.

Accordingly, it is an object of this invention to prepare a hemostasis valve unit.

Another object of this invention is to prepare a hemostasis valve which permits the easy insertion and withdrawal of catheters.

Another object of the invention is to prepare a hemostasis valve which has sufficient strength not to collapse on repeated insertions and withdrawals of catheters.

Another object of this invention is to prepare a hemostasis valve which is universal in nature and may be used with a wide variety of both large and small diameter catheters, without leakage.

Another object of this invention is to prepare a hemostasis valve which is universal in nature and which does not exert undue pressure on the side walls of an inserted catheter while still providing support for the valve in use.

It is another object of this invention to prepare a hemostasis valve which will not leak when a guidewire is inserted into a vein or artery through the valve.

It is a further object of this invention to prepare a hemostasis valve having a unitary sealing member forming at least two separate sealing sections.

It is yet another object of this invention to construct a hemostasis cannula unit which will permit the use of catheters having a wide variety of diameters, while at the same time allowing insertion of any of these catheters without undue pressure/friction thereby providing good surgical "feel" for all diameters of catheters.

These and other objectives are obtained by constructing the hemostasis cannula units of the instant invention.

SUMMARY OF INVENTION

The instant invention involves a hemostasis valve which includes a longitudinally extended housing having first and second opposing open ends; a cap means enclosing the first end and having an opening to permit insertion of a dilator or catheter into the longitudinally extended housing; and a one-piece seal means located within the central passage of the longitudinally extended housing. The seal means is provided with a sealing neck and sealing exit lips arranged so that a catheter may be readily inserted through the sealing neck and out the sealing exit lips. The sealing neck is supported by support shoulders which support the valve in use, both on the insertion of catheters or catheter introducers through the valve and on their withdrawal. The second end of the valve housing is attached to a sheath which is inserted into the vasculature.

By employing this hemostasis valve, it is possible to use different catheters which may vary in diameter. At the same time surgeons who use the universal hemostasis valve of the instant invention find that it has excellent "feel" and a reduced incidence of hemodynamic pressure dampening, for a wide range of catheter diameters. The seal means of the instant invention is particularly useful because it provides for good sealing, even around relatively small diameter catheters. This improved hemostasis valve does not collapse under use even when catheters with varying diameters are employed and surprisingly retains its ease of insertion and withdrawal because of the support shoulders adjacent to the sealing neck located on the outside surface of the seal means.

DETAILED DESCRIPTION OF INVENTION

Figure 1:
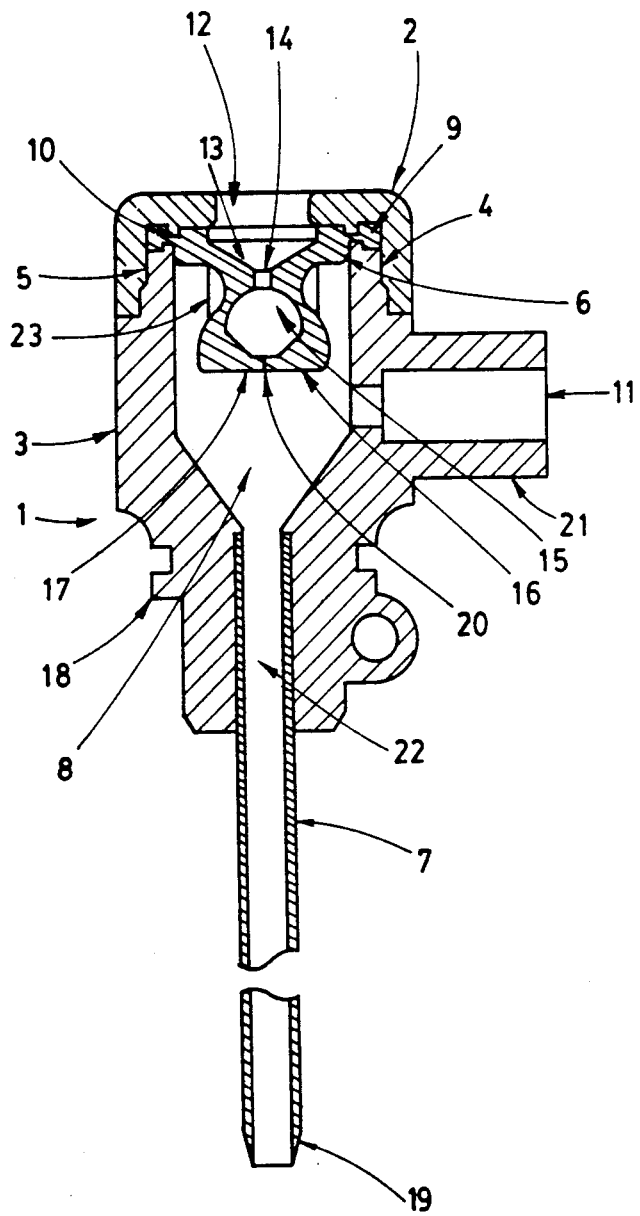
FIG. 1 is a cross-sectional view of a hemostasis valve according to the instant invention.

Turning first to FIG. 1 which shows a cross-sectional view of the hemostasis cannula unit of this invention, the cannula unit (1) is formed from four major parts. The first is the cap means (2) which is attached to the top of the longitudinally extended, valve housing (3). The valve housing has first (12) and second (22) opposing open ends to permit insertion of a catheter into and out of the interior of the valve housing (3). The cap means (2) and the valve housing (3) are formed from a relatively hard plastic such as high density polyethylene. The cap means may be secured to the valve housing by gluing or heat sealing, but preferably is mechanically attached to the valve housing using threads, clips or, as shown in the drawings, snap fittings (4) and (5). Another preferred alternative method of securing the valve housing (3) and the cap means (2) uses ultrasonic bonding. The cap means (2) and the valve housing (3) are first molded with respective interference fits and then ultrasonically bonded together. The third major element of the hemostasis cannula unit of the instant invention, the one-piece seal means (6), is formed from a pliant, resilient, rubber such as silicone rubber or latex rubber, which can be shaped to readily admit the passage of catheters. The final major element of the hemostasis cannula unit of the instant invention is a tube sheath (7) which is formed from a relatively rigid plastic such as teflon or polyethylene. The sheath is inserted within the valve housing (3) and cooperates to provide an exit from the interior (8) of the valve housing (3).

As shown in FIG. 1, the seal means (6), the cap means (2) and the valve housing (3) are joined together by inserting the seal means (6) into the cap (2) such that the upper most edge (9) of the seal means (6) is fully inserted within the cap and rests against the rib (10), which is preferably circular in nature. The cap (2) with the seal means (6) in position is then placed on top of the valve housing (3). The seal means (6) is inserted inside the valve housing (3), and downward pressure is applied to the cap means (2) thereby forcing the snap fitting (4), which is a circular ridge within the cap means, into engagement with the corresponding groove (5) on the valve housing. With the fittings (4) and (5) engaged, downward pressure on the cap (2) is maintained causing compression of the uppermost edge (9) of the seal means (6) by the rib (10) which serves to hold the seal means (6) in place within the valve housing (3).

The cap means (2) is provided with a first opening (12) at the top, which can receive the dilator (not shown) that is inserted within the hemostasis cannula unit for purposes of introduction into body vessels.

The seal means (6) has a conical receiving area (13) which tapers into a sealing neck having a neck opening (14). Taken together the conical receiving area (13) and neck opening (14) provide for easy insertion of a catheter into the seal means and through the neck opening (14), with good "feel" and a minimization of hemodynamic pressure dampening.

Communicating with the conical receiving area (13) and the neck opening (14) is a sealing chamber (15) which may be of any convenient shape, although preferably, it is semi-spherical or flatten spherical in shape. The interior diameter of the chamber (15) is preferably the same as the largest outside diameter of any catheter which will be employed with the hemostasis cannula unit of this invention. The diameter of the neck opening (14) which leads into the chamber (15) should be slightly smaller than that of any guidewire which will be employed so as to provide for sealing against the reverse flow of blood which may enter into the chamber (15) while a guidewire is in place in the cannula unit.

In order to provide support for the valve when a catheter is inserted through the neck opening (14) support shoulders (23) are located on the outside of the seal means (6) where the conical receiving area (13) tapers into the neck opening (14). See FIGS. 1 and 4. The size of the support shoulders (23) is such that the sealing means has a consistent outer diameter from the neck opening to that portion of the seal means containing the sealing chamber (15). Thus, the support shoulders do not extend outward beyond the widest portion of the sealing chamber (15) or downward around the outside surface of the sealing chamber (15) to increase the overall diameter of the seal means (6). Specifically, the support shoulders do not increase the outside diameter of that portion of the seal means containing the sealing chamber (15). Also, the support shoulders do not extend downward beyond the widest portion of the outside of the sealing chambers (15), thus avoiding undue expansion of the neck opening (14) against the side walls of the valve housing (3) upon insertion of a cannula. As a result, when a catheter is inserted through the neck opening (14), the neck area will not unduly bulge out and come into contact with the walls of the valve housing (3). The support shoulders (23) prevent the seal means extending excessively downward toward the second opposing open end (22) of the valve housing and, importantly, provide support for the seal means on insertion and removal of catheters through the seal means. Two or more support shoulders are supplied on the outside of the seal means, but preferably four support shoulders are used to provide maximum support for the seal means. When four support shoulders are used, preferably two are located perpendicular to the slit (20) and two in line with the slit (20). See FIG. 4.

The single slit (20) and the lips (16) and (17) may be forced open by a dilator or catheter inserted into the body of the hemostasis cannula unit and through the seal means (6). The spacial geometry of the walls of the semi-spherical sealing chamber (15) strongly force opposing sealing lips (16) and (17) into a normally closed position and hold them in that position to prevent an external reverse flow of blood. Likewise, when the sealing lips (16) and (17) are opened after a catheter is inserted, the opposing forces of the neck (14) will seal around the catheter and halt the reverse flow of blood.

The sealing lips which are shown in the form of a pair of opposing lips (16) and (17) may also take the form of three or four separate lips formed from either "y" or "cross" shaped slits. However, two lips are preferred because they provide the maximum amount of sealing pressure from the semi-spherical walls of the sealing chamber (15) when a catheter is not in place in the hemostasis cannula unit.

The outside diameter of the sealing chamber (15) should be less than the diameter of the longitudinally extended hemostasis valve housing so as to insure that, even upon insertion of a catheter into the seal means (6), the body of the seal means (6) will not expand against the interior walls of the valve housing thereby increasing the difficulty of catheter insertion and the likelihood of hemodynamic pressure dampening. Because of their location adjacent to the sealing neck, the sealing shoulders (23) also do not extend the diameter of the sealing chamber (15) of the seal means to the interior walls of the valve housing.

The valve housing itself (3) is longitudinally extended to form a valve chamber (8) having first (12) and second (22) openings which allow a catheter to be inserted through the chamber. Preferably access to the interior to the chamber is also provided through a port (11) to which is attached a fitting (21) that facilitates attachment of tubing to permit insertion or withdrawal of fluids from the chamber (8) during use.

The valve housing (3) of the hemostasis cannula unit is also provided with a suture ring (18) to allow temporary attachment of the cannula unit directly to a patient's body to provide stabilization of the hemostasis cannula unit.

The final element of the hemostasis cannula unit of the instant invention is the sheath (7) onto which the valve housing (3) may be attached. The sheath preferably is provided with a tapered distal tip (19), in the preferred use to closely fit onto a dilator which is inserted through the cannula for initial introduction into a body vessel.

In the preferred means of operation, a needle is inserted into a patient's blood vessel. Through the lumen of the needle a guidewire is in turn inserted into the blood vessel. The needle is removed. The hemostasis cannula unit (1) of the instant invention is then prepared by inserting a dilator through the cap opening (12), the seal means (6), out the opening (22) through the sheath (7) and out the distal tip (19) of the sheath. The sheath (7) and dilator are designed such that the distal tip (19) snugly fits around the dilator.

The dilator and hemostasis cannula unit are advanced as a unit onto the guidewire and into the blood vessel. The dilator tip, which is tapered, increases the size of the opening in the blood vessel as it enters the vessel so that ultimately an opening large enough to accommodate the sheath (7) is formed. After the sheath is inserted into the blood vessel, the dilator and guidewire are removed, leaving in place the hemostasis cannula unit of the instant invention.

With the hemostasis cannula unit, thus in place, it is possible to insert catheters having a wide range of diameters with ease. The catheter is inserted through the open end (12) or first opening in the cap means (2) and into the seal means (6). If the catheter is inserted slightly off center, it will be guided to the neck opening (14) by means of the conical receiving area (13). The catheter is then moved into the semi-spherical sealing chamber (15) and out through the sealing lips (16) and (17). After exiting through the sealing lip (16) and (17), the catheter is advanced out the open end (22) down through the sheath (7) and into the blood vessel. Any blood which flows between the sheath (7) and the catheter and up into the interior (8) of the valve housing (3) is not permitted to escape to the exterior because of the sealing action of the neck opening (14) around the body of the catheter.

Support for the seal means (6) as the catheter is being inserted, is provided by the support shoulders (23). The support shoulders (23) do not extend downward on to the outside surface of the sealing chamber (15) so that a consistent overall diameter of the seal means (6) is maintained from the neck opening (14) through the sealing chamber (15). The support shoulders (23) surprisingly reduce the insertion and withdrawal forces making insertion and withdrawal easier, providing better "feel" for the cardiologist. The support shoulders (23) also provide excellent support for the seal means (6) to prevent collapse while in use.

Figure 2:
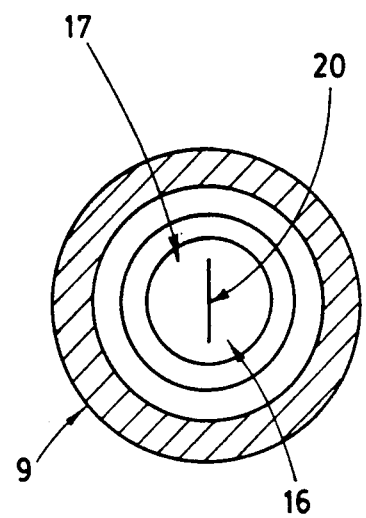
FIG. 2 is a bottom view of the one-piece, seal means of the instant invention.

In FIG. 2, which is a bottom view of the seal means of the instant invention, the sealing lips (16) and (17) are shown along with the slit (20).

Figure 3:
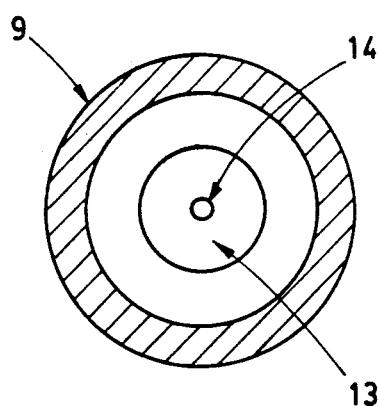
FIG. 3 is a top view of the seal means of the instant invention.

In FIG. 3, which is a top view of the seal means of the instant invention, the conical receiving area (13) of the seal means (6) is illustrated along with the neck opening (14).

Figure 4:
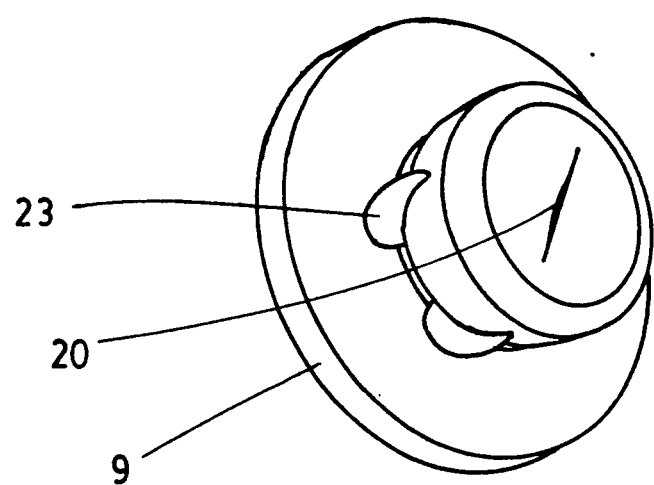
FIG. 4 is a perspective view of the seal means of the instant invention showing the support shoulders.

In FIG. 4, which is a side perspective view of the seal means of the instant invention, the support shoulders (23) and their location on the seal means (6) is disclosed.

The present embodiment of the instant invention is considered to be merely illustrative and changes may be made in its specific form without departing from the spirit or essential characteristics of this invention.

What is claimed:

1. A hemostasis cannula unit comprising:
   (a) a longitudinally extended valve housing having a first opening and a central longitudinal chamber communicating with an opposite second opening;
   (b) a cap means enclosing the first opening of the valve housing and providing a hole to permit the insertion of a catheter into the housing's first opening through the central chamber and out the opposite second opening; and
   (c) a one-piece seal means stationarily located within said central chamber and having a conical receiving area tapered into a sealing neck and communicating with said hole in said cap means, said sealing neck further communicating with a sealing chamber having sealing exit lips, wherein said seal means has support shoulders on an outside surface of said seal means adjacent to the sealing neck, wherein said support shoulders are not greater in diameter than the widest portion of the sealing chamber, and wherein the widest portion of said sealing chamber has an outside diameter less than that of said valve housing such that an annular spacing is defined between said sealing chamber and interior walls of said valve housing, said annular spacing being maintained when a catheter is inserted into said seal means and wherein said sealing exit lips are formed of at least a pair of opposing normally closed lips.

2. The hemostasis cannula unit of claim 1 wherein the valve housing includes an exit port providing access to the central chamber.

3. The hemostasis cannula unit of claim 1 wherein the sealing lips are formed from a slit in a flattened section of the sealing chamber, said slit being generally perpendicular to the axis of the longitudinally extended valve housing.

4. The hemostasis cannula unit of claim 1 wherein the sealing neck is adjacent the cap means.

5. The hemostasis cannula unit of claim 1 in combination with a sheath means.

6. The hemostasis cannula unit of claim 5 wherein the sheath means is tapered at a distal end thereof.

7. The hemostasis cannula unit of claim 1 wherein said seal means has four support shoulders.

8. The hemostasis cannula unit of claim 7 wherein the sealing means has a consistent outer diameter from the sealing neck to the sealing chamber.

* * * * *